(12) United States Patent
Xiong et al.

(10) Patent No.: US 11,045,334 B2
(45) Date of Patent: Jun. 29, 2021

(54) KNEE JOINT POWER GENERATION DEVICE BASED ON BIDIRECTIONAL BALL SCREW DRIVE AND APPLICATION THEREOF

(71) Applicant: Huazhong University of Science and Technology, Hubei (CN)

(72) Inventors: Caihua Xiong, Hubei (CN); Zhongkui Huang, Hubei (CN); Jun Fan, Hubei (CN); Wenbin Chen, Hubei (CN)

(73) Assignee: Huazhong University of Science and Technology, Hubei (CN)

( * ) Notice: Subject to any disclaimer, the term of this patent is extended or adjusted under 35 U.S.C. 154(b) by 157 days.

(21) Appl. No.: 16/448,641

(22) Filed: Jun. 21, 2019

(65) Prior Publication Data
US 2020/0100919 A1   Apr. 2, 2020

(30) Foreign Application Priority Data
Sep. 30, 2018 (CN) .......................... 201811159833.7

(51) Int. Cl.
*A61F 2/64* (2006.01)
*F03G 5/06* (2006.01)
*A61F 2/68* (2006.01)
*A61F 2/76* (2006.01)

(52) U.S. Cl.
CPC .................. *A61F 2/68* (2013.01); *A61F 2/64* (2013.01); *F03G 5/06* (2013.01); *A61F 2/76* (2013.01)

(58) Field of Classification Search
CPC .... A61F 2/64; A61F 2/68; A61H 3/00; A61H 2201/1253; A61H 2201/1261; A61H 2201/149; A61H 2201/1669; A61H 2201/1664; A61H 1/024; A61H 1/0262; B25J 9/0006; F03G 5/00; F03G 5/06; F03G 5/08
See application file for complete search history.

(56) References Cited

U.S. PATENT DOCUMENTS 10,702,441 B2 * 7/2020 Julin ........................ B25J 9/104

* cited by examiner

*Primary Examiner* — Brian A Dukert
(74) *Attorney, Agent, or Firm* — Hamre, Schumann, Mueller & Larson, P.C.

(57) ABSTRACT

The present disclosure discloses a knee joint power generation device based on bidirectional ball screw drive, and belongs to the field of biomechanical energy harvesting. The power generation device converts the rotary motion of the knee joint during human movement into a linear motion of the rope by the rope driving device, and then converts the linear motion into a rotary motion through a bidirectional ball screw to directly act on the motor, thereby converting the human biological energy into electric energy in the whole process to achieve power generation. The power generation device of the disclosure can meet the requirements of normal power generation during high-speed running and low-speed walking, has long-term high-efficiency and stable performance, can be easily worn on different people, has light overall weight and costs less loss of human walking metabolism.

8 Claims, 3 Drawing Sheets

KNEE JOINT POWER GENERATION DEVICE BASED ON BIDIRECTIONAL BALL SCREW DRIVE AND APPLICATION THEREOF

BACKGROUND

Technical Field

The disclosure belongs to the field of biomechanical energy harvesting, and more particularly relates to a power generation device capable of collecting and converting human knee joint movement energy into electric energy.

Description of the Related Art

With the rapid development of today's technology, the demand for and dependence on various electronic devices increasingly grow, especially for military personnel who are marching and fighting in the field, or those who are experiencing outdoor adventures or suffering from natural disasters, in which case they lack power and constantly walk, resulting in an urgent problem to be solved: how to find sufficient power to meet their communication, survival and operational requirements in the field for a long time.

Traditional power generation methods include solar power generation or wind power generation. However, such power generation methods are greatly affected by natural weather. Solar power generation cannot meet the demand for power generation at night, and wind power generation has high requirements for regions and climate. Therefore, it is required to develop portable power generation equipment related to the human body. Among the existing devices, the United States developed a piezoelectric shoe that uses the human walking pressure to generate electricity. Such device is simple, practical and effective, but has low power generation efficiency, which is difficult to meet actual needs. Israeli research personnel invented a backpack power generation device that uses the cyclical changes in distance between the ankle and the hip joint in human walking to generate electrical energy. Such device generates higher power, but has large overall weight, brings about large metabolic energy consumption of the human body during operation, and thus is poor in practicability.

SUMMARY

In view of the above-described defects or improvement requirements in the art, the present disclosure provides a knee joint power generation device based on bidirectional ball screw drive. Basing on the bidirectional ball screw drive, the disclosure propose a lightweight flexible and wear suitable transmission power generation scheme, which is capable of effectively increasing the generated power of the device and reducing the metabolic energy consumption to the human body, thereby solving the technical problem that the existing knee joint power generation device has low power generation efficiency, large weight, and large metabolic consumption to the human body.

In order to achieve the above objective, the present disclosure provides a knee joint power generation device based on bidirectional ball screw drive, comprising: a base plate, a shank plate, a left and right handed screw shaft, a right-handed nut, a left-handed nut, a generator, a coupling, a first guide rail connecting member, a second guide rail connecting member, a third guide rail connecting member, a fourth guide rail connecting member, a fixed pulley, a first wire rope, a second wire rope and two smooth shafts.

The two smooth shafts and the left and right handed screw shaft are parallel to each other and are fixed on the base plate, and the two smooth shafts are respectively located on two sides of the left and right handed screw shaft; the generator is fixed on the base plate and connected to an upper end of the left and right handed screw shaft through the coupling; a lower end of the base plate is pivotally connected to an upper end of the shank plate, and the fixed pulley is disposed at the pivoting portion of the base plate and the shank plate.

The left and right handed screw shaft includes a left-handed threaded section and a right-handed threaded section distributed from top to bottom, the left-handed nut is disposed on the left-handed threaded section, and the right-handed nut is disposed on the right-handed threaded section; the first guide rail connecting member and the third guide rail connecting member are fixedly connected to the left-handed nut and respectively disposed on the two smooth shafts; the second guide rail connecting member and the fourth guide rail connecting member are fixedly connected to the right-handed nut, and are respectively disposed on the two smooth shafts.

The first wire rope has an upper end fixed to the first guide rail connecting member and a lower end fixed to the shank plate through the fixed pulley; the second wire rope has an upper end fixed to the fourth guide rail connecting member and a lower end fixed to the shank plate through the fixed pulley; at least one of the first wire rope and the second wire rope is wound around the pulley by one lap.

Further, the fixed pulley is a double-layer pulley member, and the first wire rope and the second wire rope each lay one layer.

Further, the power generation device further comprises a joint connecting member, through which the shank plate is pivotally connected to the base plate; array mounting holes are provided on the shank plate, and the joint connecting member has an upper end pivotally connected to the base plate and a lower end fittingly fixed to different holes of the array mounting holes to adapt to different leg lengths.

Further, the fixed pulley, the joint connecting member and the shank plate are detachably connected to accommodate shanks with different thicknesses by adjusting the stacking order at the connecting portion.

Further, the power generation device further comprises a shank fixing side plate and a thigh fixing side plate; the shank fixing side plate is mounted on the shank plate, the thigh fixing side plate is mounted on the base plate, and both the shank fixing side plate and the thigh fixing side plate are provided with holes for mounting straps.

Further, the power generation device further comprises ball bearings, through which the first guide rail connecting member, the second guide rail connecting member, the third guide rail connecting member and the fourth guide rail connecting member are connected to the corresponding smooth shafts.

Further, the double-layer pulley member is fixedly or integrally formed with the joint connecting member.

The disclosure further provides the use of the knee joint power generation device as described above for power generation on a human elbow joint, an animal joint or a machine having a hinged structure.

In general, by comparing the above technical solution of the present inventive concept with the prior art, the present disclosure has the following beneficial effects:

1. The disclosure converts the rotary motion of the knee joint during human movement into a linear motion of the rope, and then converts the linear motion into a rotary motion through a bidirectional ball screw to directly act on the motor, thereby converting the human biological energy into electric energy in the whole process to achieve power generation. In addition, the power generation device is simple in structure and lightweight, and has good practicability.

2. The bidirectional ball screw pair can convert the axial movement of the wire rope on the nut into the rotary motion of the screw, and the left and right fixed wire ropes alternately act on the left and right handed nuts respectively, so that one-way pulling of the wire rope can drive the screw to rotate due to the characteristic of the bidirectional ball screw pair.

3. According to the device of the present disclosure, the displacement of the fixed end of the rope in each movement cycle can be changed by replacing with fixed pulleys of different radii, thereby changing the corresponding transmission ratio and then changing the generated power.

4. According to the device of the present disclosure, the transmission ratio of the power generation device can be changed by changing the lead of the bidirectional ball screw, thereby changing the power generation efficiency.

5. The power generation device of the disclosure can meet the requirements of normal power generation during high-speed running and low-speed walking, has long-term high-efficiency and stable performance, can be easily worn on different people, has light overall weight and costs less loss of human walking metabolism.

BRIEF DESCRIPTION OF THE DRAWINGS

In all figures, the same elements or structures are denoted by the same reference numerals, in which.

Figure 1:
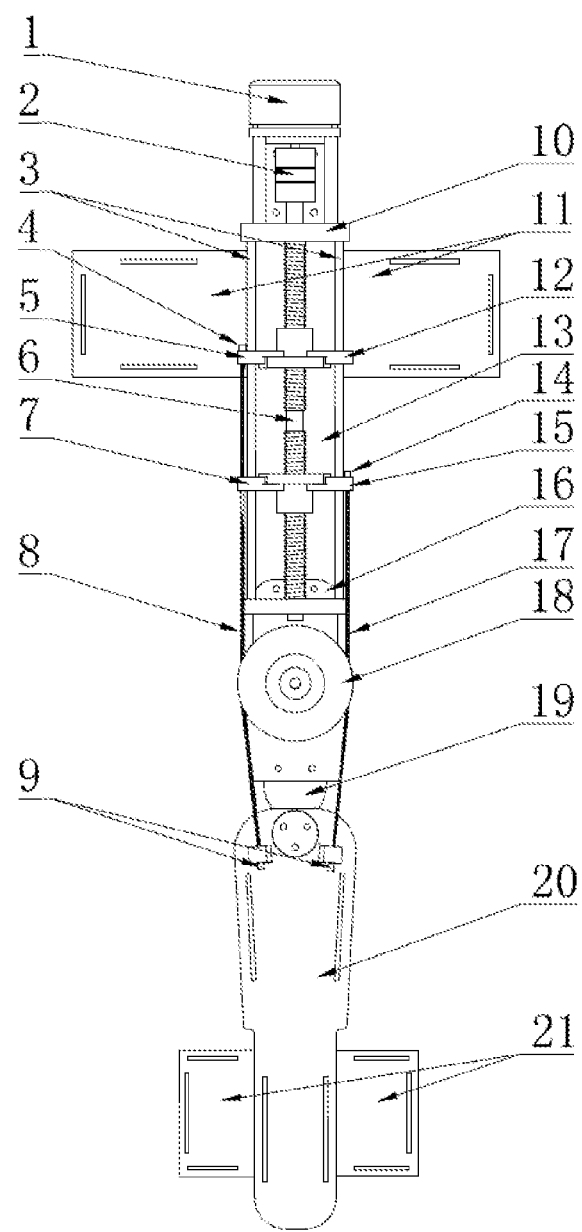
FIG. 1 shows an overall view of a power generation device according to the disclosure.

generator 1, coupling 2, smooth shaft 3, first wire rope clamping head 4, first guide rail connecting member 5, left and right handed screw shaft 6, second guide rail connecting member 7, first wire rope 8, wire rope fixing clamping head 9, connecting seat 10, thigh fixing side plate 11, third guide rail connecting member 12, base plate 13, second wire rope clamping head 14, fourth guide rail connecting member 15, screw support seat 16, second wire rope 17, double-layer pulley member 18, joint connecting member 19, shank plate 20, shank fixing side plate 21, human thigh 22, right-handed nut 23, human shank 24, left-handed nut 25, left-handed threaded section 26, and right-handed threaded section 27.

DETAILED DESCRIPTION OF THE EMBODIMENTS

For clear understanding of the objectives, features and advantages of the present disclosure, detailed description of the present disclosure will be given below in conjunction with accompanying drawings and specific embodiments. It should be noted that the embodiments described herein are only meant to explain the present disclosure, and not to limit the scope of the present disclosure. Furthermore, the technical features related to the embodiments of the disclosure described below can be mutually combined if they are not found to be mutually exclusive.

The bidirectional ball screw pair includes three parts: a left and right handed screw shaft 6 composed of a left-handed threaded section 26 and a right-handed threaded section 27, a right-handed nut 23 and a left-handed nut 25. The ball screw uses smooth shafts 3 for the rail drive, and the smooth shafts 3 include two identical smooth shafts, which are connected to the ball screw through a first guide rail connecting member 5, a second guide rail connecting member 7, a third guide rail connecting member 12, a fourth guide rail connecting member 15 and corresponding bearings to realize the function of the smooth rail. The first guide rail connecting member 5, the second guide rail connecting member 7, the third guide rail connecting member 12 and the fourth guide rail connecting member 15 have the same structure, and each have a large-diameter hole for mounting a rolling bearing and a small-diameter hole. The bearings slide on the smooth shaft 3 to ensure the smooth axial movement of the screw nuts, and the small-diameter holes on the first guide rail connecting member 5 and the fourth guide rail connecting member 15 are respectively used for mounting the first wire rope clamping head 4 and the second wire rope clamping head 14. When mounted, the first wire rope 8 passes through the second guide rail connecting member 7, and then is clamped by the first guide rail connecting member 5 at the end. The first wire rope clamping head 4 has a larger diameter than that of the small-diameter hole on the first guide rail connecting member 5, and the other ends of the first wire rope 8 and the second wire rope 17 are fixed to a boss of the shank plate 20 in the same manner to achieve tensioning of the first wire rope 8 and the second wire rope 17. When a force is applied to an end of the first wire rope 8 at the wire rope fixing clamping head 9, the first wire rope clamping head 4 is pulled to push the first guide rail connecting member 5 to move downward, thereby driving the rotation of the bidirectional ball screw. Similarly, when a force is applied to an end of the second wire rope 17 at the wire rope fixing clamping head 9, the second wire rope clamping head 14 is pulled to push the fourth guide rail connecting member 15 to move downward, thereby driving the rotation of the bidirectional ball screw. The left and right handed screw shaft 6 and the generator 1 are positioned by a connecting seat 10 and a corresponding bearing to ensure coaxiality, and are fixedly connected by a coupling 2 at the shaft end. The other end of the ball screw is supported by a screw support seat 16 and a corresponding bearing, and the connecting seat 10 and the screw support seat 16 are fixed a base plate 13.

Figure 3:
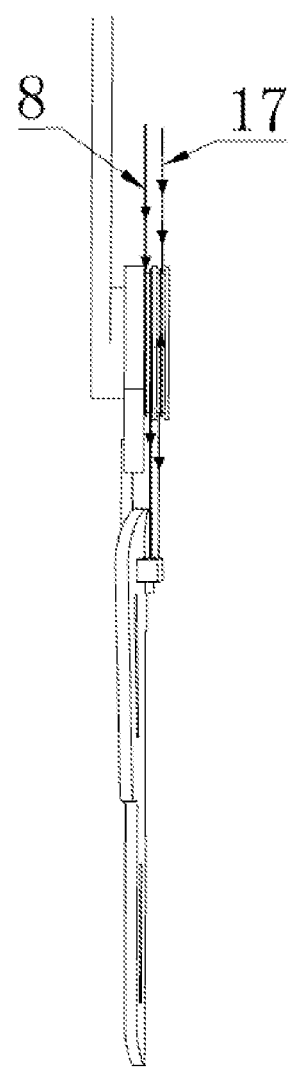
FIG. 3 shows winding manners of the wire ropes in a double-layer pulley member 18.

The double-layer pulley member 18 is mounted on the base plate 13 and has a revolute function. The double-layer pulley member 18 is similarly formed by stacking two fixed pulleys. FIG. 3 is a side view showing winding manners of the first wire rope 8 and the second wire rope 17 on the double-layer pulley member 18. The first wire rope 8 is wound in the lower layer (left side) groove of the double-layer pulley member 18 by one lap, and then is fixed by the wire rope fixing clamping head 9. The second wire rope 17 is wound in the upper layer (right side) groove of the double-layer pulley member 18 by one lap, and then is fixed by the wire rope fixing clamping head 9. The double-layer pulley member 18 is provided with two holes configured to be fixedly connected to the joint connecting member 19 so as to directly transmit the power generated by the shank. The joint connecting member 19 is used to connect the base plate 13 on the thigh to the shank plate 20 on the shank, and when used, the shank plate 20 is mounted on the human shank. The thigh fixing side plate 11 is mounted on the base plate 13, has a rotatable revolute and thus can rotate to some extent. Slots on the thigh fixing side plate 11 are used for mounting the strap to fix the thigh fixing side plate 11 to the human thigh, and the shank fixing side plate 21 is mounted on the shank plate 20. Further, the shank fixing side plate 21 can be movably connected to the shank plate 20, for example, can be rotated around the connecting portion to be suitable for persons with different leg thicknesses. In other embodiments (not shown), the shank fixing side plate 21 can be adapted to different leg thicknesses by directly adjusting the strap tightness and length. Slots on the shank fixing side plate 21 are used for mounting the strap to fix the shank fixing side plate 21 to the human shank.

Figure 2:
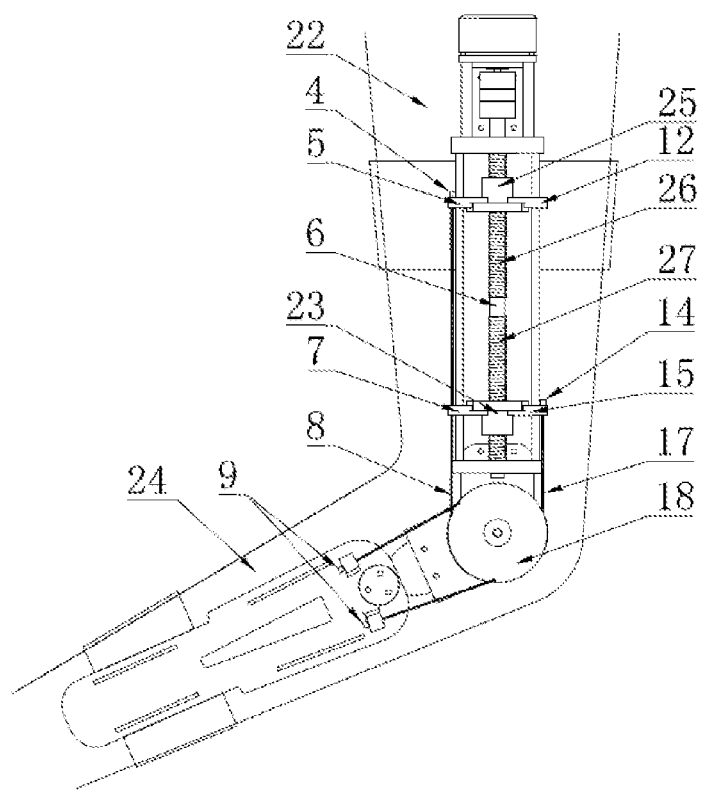
FIG. 2 shows a schematic diagram of the power generation device being worn on the human right leg and operating according to the disclosure; it should be noted that the device is also suitable for the left leg to wear, and as long as the screw stroke is sufficient, the device can meet the interchangeable use on the left and right legs.

FIG. 2 shows a first embodiment of the present disclosure. The power generation device is fixed to the thigh and the shank of the human right leg by the thigh fixing side plate 11, the shank fixing side plate 21 and the straps. During the human walking, when the right leg performs a knee flexion movement, the human shank drives the shank plate 20 to rotate clockwise, thereby driving the double-layer pulley member 18 to rotate clockwise. Since the lower end of the second wire rope 17 is fixed by the wire rope fixing clamp head 9 and cannot move, the second wire rope 17 is further wound around the double-layer pulley member 18. Since the upper end of the second wire rope 17 is fixed to the fourth guide rail connecting member 15 by the second wire rope clamping head 14 and the fourth guide rail connecting member 15 is connected to the right-handed nut 23, the right-handed nut 23 will be pulled downward when the second wire rope 17 is further wound, thereby driving the rotation of the whole left and right handed screw shaft 6 and then driving the generator 1 through the coupling 2 to rotate and generate electricity. At the same time, the rotation of the left and right handed screw shaft 6 will drive the movement of the left-handed nut 25, and since the direction of rotation of the left-handed threaded section 26 corresponding to the left-handed nut 25 is opposite to that of the right-handed threaded section 27 corresponding to the right-handed nut 23, the left-handed nut 25 has an opposite movement direction to that of the right-handed nut 23, that is, moves upward. The upward movement of the left-handed nut 25 pulls the first wire rope clamping head 4 and then pulls the first wire rope 8 to be stretched upward, so that the first wire rope 8 which is relaxed due to the clockwise rotation of the double-layer pulley member 18 is continuously tightened. FIG. 2 shows a state in which the knee joint of the right leg flexes at a certain angle, and compared with the standing initial state of in FIG. 1, the left-handed nut 25 moves upward, the right-handed nut 23 moves downward, the first wire rope 8 is wound around the double-layer pulley member 18 by less than one lap, and the second wire rope 17 is wound around the double-layer pulley member 18 by more than one lap.

When the human leg completes the knee flexion movement, it begins to enter the stretching phase of the knee joint. The human shank drives the shank plate 20 to rotate counterclockwise, thereby driving the double-layer pulley member 18 to rotate counterclockwise. In this case, the first wire rope 8 starts to be further wound in the groove of the pulley under the rotation of the double-layer pulley member 18, while the second wire rope 17 begins to reduce the winding contact surface. The winding of the first wire rope 8 pulls the first wire rope clamping head 4 to move downward, and then pulls the left-handed nut 25 to move downward, thereby driving the rotation of the whole left and right handed screw shaft 6 and then driving the generator 1 through the coupling 2 to rotate and generate electricity. At the same time, the rotation of the left and right handed screw shaft 6 will drive the right-handed nut 23 to move upward, pull the second wire rope clamping head 14 and then pull the second wire rope 17 to be stretched upward, so that the second wire rope 17 which is relaxed due to the counterclockwise rotation of the double-layer pulley member 18 is continuously tightened. The state returns to the standing initial state as shown in FIG. 1 after a certain movement process, in which the symmetrical central axis of the base plate 13 is in line with the symmetrical central axis of the shank plate 20, and both the first wire rope 8 and the second wire rope 17 are wound around the double-layer pulley member 18 by one lap. The above embodiment is a description of a gait cycle of the human movement.

Further, the device of the present disclosure can also be suitable for the left leg to wear, and the interchangeable use on the left and right legs can be realized. When the device is worn on the left leg and the knee flexion movement is performed, the shank plate will rotate counterclockwise relative to the state of FIG. 1, thereby driving the first wire rope 8 to move downward and causing the generator to generate electricity. When the device is worn on the left leg and the stretching movement is performed, the shank plate will rotate clockwise, thereby driving the second wire rope 17 to move downward and causing the generator to generate electricity. Further, as long as the strokes of the left-handed threaded section 26 and the right-handed threaded section 27 are sufficiently large, the device of the present disclosure can meet the interchangeable use on the left and right legs. When the knee joint continuously moves, the device of the present disclosure will continuously reciprocate to generate electricity. Further, the voltage generated by the device of the present disclosure is an alternating voltage, since the rotation directions of the screw during the knee flexion and stretching movements are different.

Further, in order to ensure the normal operation of the device of the present disclosure, it is necessary to ensure that a distance between center lines of the first wire rope 8 and the second wire rope 17 to a center line of the left and right handed screw shaft 6 is equal to a distance from the wire rope wound around the double-layer pulley member 18 to the center of the double-layer pulley member 18.

Further, the device of the present disclosure can change the generating capacity as needed. Specifically, the transmission ratio of the device of the present disclosure can be changed as needed, and the transmission ratio of the device of the present disclosure can be increased by increasing the diameters of the grooves of the double-layer pulley member 18 to increase the generated power in each gait cycle and then increase the generated power of the device.

Further, the transmission ratio of the device can also be changed by selecting bidirectional ball screws with different leads to increase the generated power. Increasing the lead of the bidirectional ball screw will increase the transmission ratio of the device and then increase the generated power of the device.

Further, the base plate 13 and the shank plate 20 are pivotally connected by the joint connecting member 19. For persons having different leg shapes and thicknesses, the plane difference between the base plate 13 and the shank plate 20 can be adjusted by selecting mounting surfaces of the joint connecting member 19 on the base plate 13 and the shank plate 20 to adapt to persons having different leg thicknesses. Specifically, FIG. 1 shows a mounting method for persons with normal thick legs, in which one end of the joint connecting member 19 is mounted on the lower surface of the double-layer pulley member 18 and the other end of the joint connecting member 19 is mounted on the lower surface of the shank plate 20. For persons with thick legs, one end of the joint connecting member 19 is mounted on the upper surface of the double-layer pulley member 18 and the other end of the joint connecting member 19 is mounted on the on the lower surface of the shank plate 20. For persons with large thick difference between the thigh and the shank, a spacer can be added for adjustment.

Further, the device of the present disclosure is not limited to use for the human knee joint. For other human active joints such as the elbow joint, the device can be applied to generate electricity. The same effect can also be achieved by mounting the device on a machine with a hinged structure or an animal joint.

It should be readily understood to those skilled in the art that the above description is only preferred embodiments of the present disclosure, and does not limit the scope of the present disclosure. Any change, equivalent substitution and modification made without departing from the spirit and scope of the present disclosure should be included within the scope of the protection of the present disclosure.

What is claimed is:

1. A knee joint power generation device based on bidirectional ball screw drive, comprising:
    a base plate, a shank plate, a left and right handed screw shaft, a right-handed nut, a left-handed nut, a generator, a coupling, a first guide rail connecting member, a second guide rail connecting member, a third guide rail connecting member, a fourth guide rail connecting member, a fixed pulley, a first wire rope, a second wire rope and two smooth shafts; wherein
    the two smooth shafts and the left and right handed screw shaft are parallel to each other and are fixed on the base plate, and the two smooth shafts are respectively located on two sides of the left and right handed screw shaft;
    the generator is fixed on the base plate and connected to an upper end of the left and right handed screw shaft through the coupling;
    a lower end of the base plate is pivotally connected to an upper end of the shank plate, and the fixed pulley is disposed at the pivoting portion of the base plate and the shank plate;
    the left and right handed screw shaft includes a left-handed threaded section and a right-handed threaded section distributed from top to bottom, the left-handed nut is disposed on the left-handed threaded section, and the right-handed nut is disposed on the right-handed threaded section;
    the first wire rope has an upper end fixed to the first guide rail connecting member and a lower end fixed to the shank plate through the fixed pulley;
    the second wire rope has an upper end fixed to the fourth guide rail connecting member and a lower end fixed to the shank plate through the fixed pulley; and
    at least one of the first wire rope and the second wire rope is wound around the pulley by one lap.

2. The knee joint power generation device based on bidirectional ball screw drive according to claim 1, wherein the fixed pulley is a double-layer pulley member, and the first wire rope and the second wire rope each occupy one layer.

3. The knee joint power generation device based on bidirectional ball screw drive according to claim 1, further comprising:
    a joint connecting member, through which the shank plate is pivotally connected to the base plate; and
    array mounting holes provided on the shank plate,
    wherein the joint connecting member has an upper end pivotally connected to the base plate and a lower end fittingly fixed to different holes of the array mounting holes to adapt to different leg lengths.

4. The knee joint power generation device based on bidirectional ball screw drive according to claim 3, wherein the fixed pulley, the joint connecting member and the shank plate are detachably connected to accommodate shanks with different thicknesses by adjusting the stacking order at the connecting portion.

5. The knee joint power generation device based on bidirectional ball screw drive according to claim 1, further comprising:
    a shank fixing side plate; and
    a thigh fixing side plate;
    wherein the shank fixing side plate is mounted on the shank plate, the thigh fixing side plate is mounted on the base plate, and both the shank fixing side plate and the thigh fixing side plate are provided with holes for mounting straps.

6. The knee joint power generation device based on bidirectional ball screw drive according to claim 1, further comprising:
    ball bearings through which the first guide rail connecting member, the second guide rail connecting member, the third guide rail connecting member and the fourth guide rail connecting member are connected to the corresponding smooth shafts.

7. The knee joint power generation device based on bidirectional screw drive according to claim 1, wherein the device is worn on a human joint or an animal joint to generate electricity.

8. The use of the knee joint power generation device based on bidirectional screw drive according to claim 2, wherein the double-layer pulley member is fixedly or integrally formed with the joint connecting member.

* * * * *